United States Patent [19]

Tom

[11] Patent Number: 5,260,585
[45] Date of Patent: Nov. 9, 1993

[54] ENDPOINT AND/OR BACK DIFFUSION GAS IMPURITY DETECTOR, AND METHOD OF USING THE SAME

[75] Inventor: Glenn M. Tom, New Milford, Conn.

[73] Assignee: Novapure Corporation, Danbury, Conn.

[21] Appl. No.: 898,840

[22] Filed: Jun. 12, 1992

[51] Int. Cl.⁵ .......................................... G01N 15/06
[52] U.S. Cl. .................................... 250/573; 340/540
[58] Field of Search ............... 250/573; 340/632, 633, 340/634, 540; 423/210, 588; 502/400, 401; 55/36; 73/31.02, 28.02, 29.05, 31.05

[56] References Cited

U.S. PATENT DOCUMENTS

| 3,924,219 | 12/1975 | Braun | 73/31.05 |
|---|---|---|---|
| 4,603,148 | 7/1986 | Tom | 521/31 |
| 4,604,270 | 8/1986 | Tom | 423/262 |
| 4,659,552 | 4/1987 | Tom | 423/219 |
| 4,723,967 | 2/1988 | Tom | 55/36 |
| 4,738,693 | 4/1988 | Tom | 55/36 |
| 4,761,395 | 8/1988 | Tom | 502/401 |
| 4,781,900 | 11/1988 | Tom et al. | 423/210 |
| 4,782,226 | 11/1988 | Jeffries et al. | 250/227 |
| 4,797,227 | 1/1989 | Tom et al. | 252/194 |
| 4,800,189 | 1/1989 | Eschwey et al. | 502/400 |
| 4,847,594 | 7/1989 | Stetter | 340/540 |
| 4,853,148 | 8/1989 | Tom et al. | 252/194 |
| 4,865,822 | 9/1989 | Tom et al. | 423/210 |
| 4,925,646 | 5/1990 | Tom et al. | 423/488 |
| 4,950,419 | 8/1990 | Tom et al. | 252/194 |
| 4,983,363 | 1/1991 | Tom et al. | 422/180 |
| 5,015,411 | 5/1991 | Tom et al. | 252/194 |

FOREIGN PATENT DOCUMENTS

| 299488 | 1/1989 | European Pat. Off. . |
|---|---|---|
| 365490 | 4/1990 | European Pat. Off. . |
| 449791 | 2/1991 | European Pat. Off. . |
| 438036 | 7/1991 | European Pat. Off. . |
| 470936 | 2/1992 | European Pat. Off. . |

OTHER PUBLICATIONS

R. C. West, ed., CRC Handbook of Chemistry and Physics, 65th ed., CRC Press, Boca Raton, Fla., pp. D155-D159 (1984).
"Chlorination of silanes by silver chloride," Vanderwielen, A. J., Ring, M. A., Inorg. Chem. 11(2), pp. 246–250 (1972).
"Halogenation of silanes by silver chloride and silver bromide," Hollandsworth, R. P., et al., Inorg. Chem. 6(4), pp. 844–845 (1967).

Primary Examiner—David C. Nelms
Assistant Examiner—K. Shami
Attorney, Agent, or Firm—Steven J. Hultquist

[57] ABSTRACT

An endpoint detector for gas purifiers which contains a detection element comprising a small amount of a highly reactive metal coated on an insulator and exposed to the gas stream being purified. This metal does not react with the gas being purified, but does undergo reaction with the impurity species. As this metal reacts with impurities in the gas stream, its conductivity decreases. The change in conductivity signals that the wave front of impurity-containing gas has reached the sensor, and thus the purifier has reached the end of its useful life. The use of a thin coating of reactive metal as the detection element gives the sensitivity that is required to sense sub-part-per-million levels of impurities. This resistance change sensor may be combined with a thermal measurement to detect the presence of exothermic conditions indicative of a large pulse of impurity gas.

34 Claims, 12 Drawing Sheets

ENDPOINT AND/OR BACK DIFFUSION GAS IMPURITY DETECTOR, AND METHOD OF USING THE SAME

BACKGROUND OF THE INVENTION

1. Field of the Invention

The present invention relates to a means and method for detecting impurity concentration in a flowing gas stream, thereby to determine the end of a useful life of a gas purifier. The detection method can also be used to monitor gas lines for back-diffusion of an impurity species into the gas supply system.

2. Description of the Related Art

The rapid expansion of vapor-phase processing techniques, e.g., chemical vapor deposition, in the semiconductor industry has been associated with the deployment and use of manufacturing equipment that is totally reliant on the delivery of ultra-high purity process gases at the point of use in the semiconductor manufacturing facility. Currently, over 5 billion dollars worth of such equipment is in use.

Considering the impurities which are present in gas streams involved in semiconductor manufacturing, it is to be noted that the growth of high quality thin film electronic and opto-electronic cells by chemical vapor deposition or other vapor-based techniques is inhibited by a variety of low-level process impurities. These impurities can cause defects that reduce yields by increasing the number of rejects, which can be very expensive. These impurities may be particulate or chemical contaminants. Particulates are typically filtered out of the gas stream using extremely efficient commercially available particle filters, with particle filtration generally being employed at the point of use.

Chemical impurities may originate in the production of the source gas itself, as well as in its subsequent packaging, shipment, storage, and handling. Although source gas manufacturers typically provide analyses of source gas materials delivered to the semiconductor manufacturing facility, the purity of such gases may change because of leakage into or outgassing of the containers, e.g., gas cylinders, in which the gases are packaged. Impurity contamination may also result from improper gas cylinder changes, leaks into downstream processing equipment, or outgassing of such downstream equipment.

Chemical impurities that are of special concern in semiconductor manufacturing processes include water, oxygen, other oxidant species, and Lewis acids such as aluminum, boron or zinc-containing species. For some processes, impurities that may form active doping species in the resultant film are of concern, such as phosphorus or arsenic species in silicon processes. In general, the key chemical impurities must be held at levels of a few parts per billion or lower.

In support of the requirement for high purity process gases, a number of types of gas purifiers have been introduced that remove chemical contaminants from the semiconductor process gases at the point of use. These gas purifiers employ a variety of sorption processes to remove impurities, including physisorption processes, e.g. gas adsorption by zeolites or activated carbon, or various chemisorption processes, where the impurities adsorb to and chemically react with a component or components of the purifier.

Particularly useful in-line purifiers are based on sorption processes, wherein the impurity species are adsorbed and chemically reacted with scavengers bound to or incorporated in porous inert support materials. Such purifiers are described in U.S. Pat. Nos. 4,603,148, 4,604,270, 4,659,552, 4,761,395, 4,853,148, 4,797,227, 4,781,900, 4,800,189, and 4,950,419. This class of purifiers is quite versatile, since the immobilized scavenger may be varied and tailored to react with a large number of different impurities. Because the support material is usually porous, contact of the scavenger with the gas stream is extensive. Such gas purifiers are used to remove impurity species such as water, oxygen, other oxidant species, and Lewis acids, which have deleterious effects on the semiconductor manufacturing process. By varying the chemical identity of the scavenger, they may also be used to remove undesirable dopant species from the gas stream. For example, in silicon processing, arsenic and phosphorus are very active dopants, and thus traces of arsine and phosphine must be removed from silane, which may be the silicon source gas. European Patent Application EP 299,488 describes a metalated macroreticulate polymer having pendant functional groups used to remove arsine and phosphine impurities from silane gas.

Purifiers based on other sorption principles such as metal eutectic alloy getters are also employed. For example, European Patent Application EP 470,936 describes removal of impurities from hydride gases by passing the hydride gas over a hydrogenated getter metal in a chamber. In particular, disiloxane may be removed from silane using hydrogenated Zr-V-Fe getter alloy. Gases which may be purified in this fashion include $SiH_4$, $GeH_4$, $NH_3$, $AsH_3$, $SbH_3$ and $PH_3$, all of which are used in semiconductor manufacturing. European Patent Application EP 365,490 describes a method for removing impurity gases from inert gases such as argon or nitrogen using a first sorbent of either a non-evaporable getter alloy of Zr-V-Fe or Zr-Fe and a second sorbent of a non-evaporable getter alloy of 5-30% Al, balance Zr. Both sorbents are pellets formed from alloy powder of average particle size below 125 microns, with the first sorbent being located at the gas inlet and the second at the gas outlet.

While the gas purifiers of the types described above are very effective at removing impurities from the process gas streams to very low levels, as they become saturated, they lose their ability to remove further impurities. The operator of the semiconductor manufacturing process needs to be able to determine when the gas purifier is no longer able to provide the level of purification efficiency required. The point at which the purifier is exhausted and needs to be exchanged for a new unit is referred to as the purifier's endpoint.

If the endpoint of the purifier is not detected and the purifier is not promptly replaced, the result can be that a large number of wafers undergo vapor-phase processing before it is recognized that compositional changes in the process gas stream flowed to the reactor are leading to high rates of rejection. Such high rates of rejection in turn significantly lower the efficiency and productivity of the semiconductor manufacturing plant, and generate substantial losses of potential product. The resulting off-spec microcircuitry articles thus constitute scrap which must be reworked, if this is even feasible, or else discarded as waste.

Adsorption-type purifiers can also be used in the back-diffusion scrubbing mode, whereby the purifier serves as an impurity scrubber that protects the gas supply against contamination caused by diffusion of one or more foreign components back into the supply lines. Back-diffusion can occur when mechanical components such as check valves and shut-off valves fail. Additionally, in low flow conditions, impurities can successfully diffuse against the convective forward flow. An example of a situation where back-diffusion is of concern is the case where an inert gas such as nitrogen is used to pressurize vessels containing liquids used in semiconductor manufacturing processes. Such liquids include sulfuric acid, isopropanol, acetone and the like, which can cause corrosion and contamination of the nitrogen supply system by back-diffusion under low flow conditions.

When the purifier is used for a back-diffusion scrubber, endpoint detection is critical. Back-diffusion is not planned for, and therefore it is impossible to predictively calculate the purifier's lifetime on the basis of flowrates, expected impurity concentrations, and so forth. Endpoint detection allows the immediate detection of a serious back-diffusion event, and the appropriate precautions to protect the gas supply may be mobilized. Use of two endpoint detectors disposed at separate points in the gas purifier's scavenger bed allows back-diffusion to be distinguished from normal exhaustion of the purifier. If the downstream endpoint detector signals purifier depletion before the upstream one does, back-diffusion can be diagnosed in a straightforward and simple way.

Accordingly, there is a pressing need in the semiconductor manufacturing industry to provide commercially viable systems for continuously monitoring the performance of gas purifiers to detect the purifier endpoint. Such endpoint detectors should preferably provide a signal that can be used, upon exhaustion of the purifier, to not only alert the operator that the purifier must be replaced, but also trigger steps, such as gas input valve closing or diversion of the input gas flow through a back-up purifier, to protect the semiconductor manufacturing process from contamination.

Such an endpoint detection method should not require the use of extremely specialized equipment or highly qualified personnel and should not be subject to effects due to unknown variations in impurity levels of the gas to be purified. The detection means should show a large and rapid response to the presence of the undesirable impurities in the gas stream, with reaction occurring in a time period that is short by comparison with the rate of movement of the impurity-containing front through the gas purifier.

The response should be easily converted to an electrical signal which can be used to, for example, close and/or open a relay and thereby trigger closing of a gas supply valve or diversion of the gas stream. The detector would desirably be sensitive to broad classes of impurities, and therefore be widely useful in various semiconductor manufacturing processes. In addition, the detector would preferably be inexpensive and constructed of materials that are compatible with semiconductor processing.

In an effort to provide an endpoint detector for gas purifiers used in semiconductor manufacturing processes, European Patent Application No. EP EP 438,036 describes a system for determination of the endpoint of an inert gas purifier containing gas sorbing material by measuring the inert gas pressure at the purifier inlet and outlet. An electronic measuring device records the difference between the measured values for electronic comparison with a predetermined value and a signal is given when the difference exceeds this value to indicate the end of the purifier's useful life. The gas sorbing materials are, for example, Zr, V and Fe-containing alloys for purification of He, Ne, Ar, Kr, and Xe. Unfortunately this method, based on differences in pressure, requires the use of costly pressure measuring instruments and electronic circuitry, whose use can only be justified for large scale gas purification plants. When smaller scale gas purification units such as in-line purifiers are used, whose throughput of gas is smaller, on the order of about 10 liters per minute, it is necessary to have a reliable indication of the approach of the endpoint, but also a reduced cost. Additionally, not all gas purifiers develop an increased pressure drop as they approach endpoint. This phenomenon is limited to purifiers of the metal alloy getter type.

To the same end, European Patent Application No. EP 449,791 describes a method and apparatus for determining the end of the useful life of a gas purifier which comprises (a) a gas purifier having an impure gas inlet in fluid communication with a housing containing a gas sorbing material; (b) the housing being in fluid communication with a purified gas outlet; characterized by (c) measuring the electrical resistance (Rx) between a predetermined point within the gas sorbing material and the housing; (d) comparing (Rx) with a predetermined resistance value (Rp); and (e) indicating when Rx is greater than or equal to Rp thus indicating that the gas purifier has reached its end of useful life. This method is only useful when the gas sorbing material is a material with high conductivity, such as a metal alloy getter, and when the conductivity of the gas sorbing material is significantly changed by the process of impurity scrubbing.

The method of European Patent Application No. EP 449,791 is not broadly applicable to the adsorption type purifier exemplified by U.S. Pat. No. 4,761,395. In this adsorption type of purifier, the gas sorbing material comprises a scavenger immobilized on an inert support material such as polystyrenedivinylbenzene copolymer or an activated alumina. Such a gas sorbing material has a very low conductivity when it is new, and as the purifier is exhausted, the conductivity does not change significantly. This adsorption type of purifier is widely used, since unlike the metal alloy getter purifier, it may be used at ambient temperature rather than needing to be heated to high temperatures. It is also more versatile, since the immobilized scavenger may be tailored to a large number of impurities, whereas the metal alloy getter purifier is limited to removal of those species that react with the heated metal alloy.

Other methods have been proposed which are based on changes in physical properties of the material which sorbs the impurity gas, such as, for example, a change in color. Such a system is presented in U.S. Pat. No. 4,782,226, which describes a method for determining the exhaustion of adsorption type purifier resin beads. A tube extends inside the purifier container having a transparent bulb sealed about its end. A fiber optic probe containing a transmitting and a receiving cable is positioned inside the tube such that the ends of the cables are proximate to the inner surface of the bulb. The cables are connected to a transmitter and receiver. A light beam is transmitted through the bulb, and is then reflected by the purifier resin beads. The receiving cable receives the reflected light and returns it to the transmitter and receiver. The transmitter and receiver compares the intensity of the reflected light received with the intensity of the original transmitted light. The fully reacted resin beads have a different reflectance value than the fresh beads, so when the reaction has taken place next to the bulb, the transmitter and receiver will sense the change. Upon sensing a change, the transmitter and receiver will activate a warning device, such as a light, which informs the operator that the reaction has been completed and the purifier needs replacing. This system has the disadvantage that not all gas purifiers undergo a color change upon exhaustion. For example, back-diffusion of arsine into many resin-based purifiers, e.g. the type described in U.S. Pat. No. 4,603,148, causes an insuffient color change. In addition, the fiber optics detector and its associated electronics are fairly complex.

In the context of other industrial processes, such as internal combustion engines, a variety of means and methods have been developed for in situ oxygen and moisture sensing. Most methods provide a response in the form of an electrical signal. The detection element is usually a gas-sensing metal oxide or semiconductor. For the purifier endpoint application, these methods suffer from several deficiencies. Many require elevated temperatures, such as tin oxide oxygen sensors. Because in these other applications, the sensor is expected to respond reversibly, the size of the signal and speed of the response are not sufficient for the endpoint application. In applications where the sensor is expected to be reversible, physically robust and have a long useful life, these constraints dictate against the type of high sensitivity detector of the present invention.

The presence of even small concentrations of impurity species in the process gas streams employed in semiconductor manufacturing is potentially deleterious. Even small levels of impurities on the order of parts per million (ppm) can cause inconsistent electrical properties in semiconductor devices manufactured by deposition techniques using impurity-containing gas streams.

It therefore is an object of the present invention to provide a simple, rapid, sensitive, and versatile system for detecting the point when a gas purifier is no longer able to provide a high level of purification efficiency, such as is required to protect semiconductor manufacturing processes. It is a further object of the present invention to provide a usable signal that, upon endpoint detection, can be used to activate processes such as valve closing or gas stream diversion, that protect the integrity of the manufacturing process or gas supply system.

SUMMARY OF THE INVENTION

The present invention relates in one aspect to an endpoint detector for gas purifiers which contains a detection element comprising a small amount of a highly reactive sensor material which reacts with an impurity to yield a reaction product of changed electrical characteristic. In one preferred embodiment, the sensor material is a metal coated on an insulator and exposed to the gas stream being purified. This metal does not react with the gas being purified, but does undergo reaction with the impurity species. As this metal reacts with impurities in the gas stream, its conductivity decreases. The change in conductivity signals that the wave front of impurity-containing gas has reached the sensor, and thus the purifier has reached the end of its useful life. The use of a thin coating of reactive metal as the detection element gives the sensitivity that is required to sense sub-part-per-million levels of impurities. This resistance change sensor may be combined with a thermal measurement to detect the presence of a large pulse of impurity gas.

DETAILED DESCRIPTION OF THE INVENTION

Figure 1:
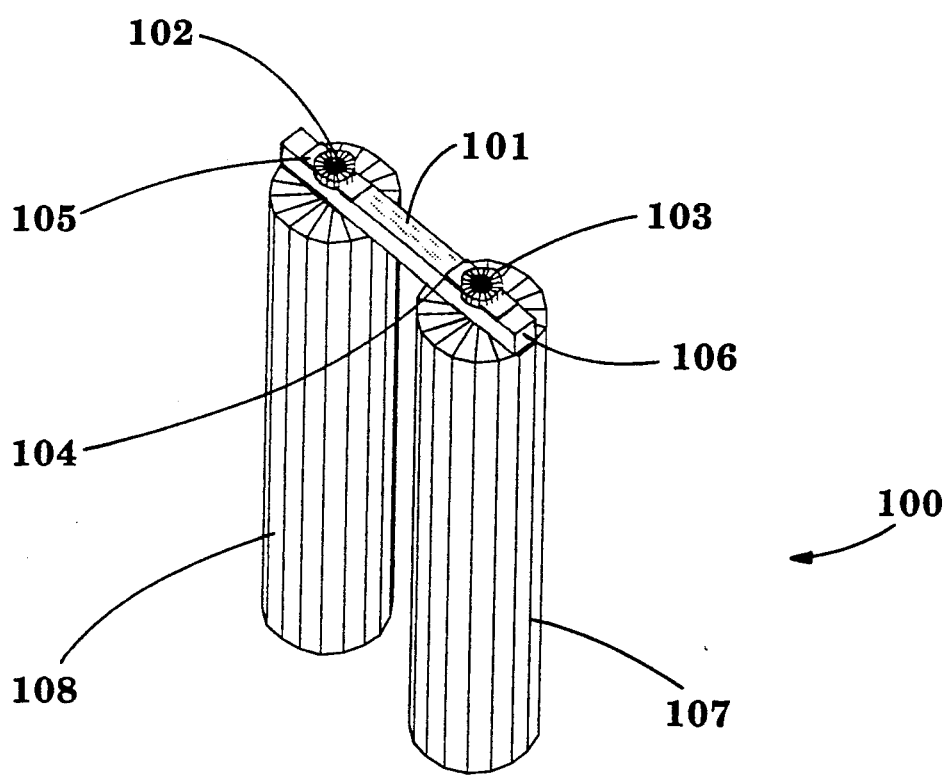
FIG. 1 shows a schematic of an endpoint detector system according to one embodiment of the present invention.

The present invention overcomes the deficiencies of the prior art endpoint detector systems, as described in the "Background of the Invention" section hereof, by the provision of a sensing system which is specifically adaptable for use in the manufacture of semiconductor devices including vapor deposition based processes.

The endpoint detector system of the present invention enables detection of the point when a gas purifier is no longer able to provide a high level of purification efficiency and provides an electrical signal which may be used to sound an alarm, light a warning light, or trip a relay which closes a gas supply valve or diverts a gas stream to an alternate flow pathway. Since the endpoint detector of the present invention responds directly to the impurity species in the gas stream and not to a change in physical properties of the purification medium, it is extremely versatile and may be used in any of the available types of in-line gas purifier.

Examples of gas purification systems which may be usefully employed in conjunction with the end-point detector systems of the present invention include the purifier apparatus, compositions, and methods disclosed and claimed in U.S. Pat. Nos. 4,761,395 (composition for purification of arsine, phosphine, ammonia and inert gases); 4,853,148 (hydrogen halide purification); 4,797,227 (hydrogen selenide purification); 4,781,900

(method of purifying arsine, phosphine, ammonia and inert gases); 4,950,419 (inert gas purification); 4,685,822 (hydrogen selenide purification); 4,925,646 (hydrogen halide purification method); 4,983,363 (apparatus for purifying arsine, phosphine, ammonia and inert gases); and 5,015,411 (inert gas purification method); as well as the purifier vessel apparatus disclosed and claimed in U.S. Pat. Nos. 4,723,967 and 4,738,693, all which hereby are incorporated herein by reference.

The present invention relates in one aspect to an endpoint detector comprising a small amount of a highly reactive sensor material which reacts with an impurity to yield a reaction product of changed electrical characteristic. The sensor material can be a metal coated on an insulator and exposed to the gas stream being purified. This metal does not react with the gas being purified, but does undergo reaction with the impurity species. As this metal reacts with impurities in the gas stream, its conductivity decreases. The change in conductivity signals that the wave front of impurity-containing gas has reached the sensor, and thus the purifier has reached the end of its useful life. Electrical measurements are capable of high sensitivity, and the use of a thin coating of reactive metal as the detection element gives the sensitivity that is required to sense sub-part-per-million levels of impurities. This resistance change sensor may be combined with a thermal measurement to detect the presence of a large pulse of impurity gas.

The dimensions of the sensor material may be varied to suit the requirements of the application in terms of sensitivity needed, size of gas purifier, etc., and are not critical to the present invention. A relatively thin layer of sensor material, on the order of 0.5 to 500 $\mu$m is useful, with thicknesses from 20-100 $\mu$m being preferred. For commonly used inline gas purifiers, the size of the sensor element may be on the order of 1 to 4 mm wide by 1 to 4 mm long and 20 to 100 $\mu$m thick.

The purity of the sensor material is only important insofar as impurities present in the sensor material must not interfere with the electrical characteristic being monitored and must not contaminate the gas stream being purified. If a reactive metal is used as the sensor material, it need not be highly elementally pure, but must not contribute volatile impurities to the gas stream. A reactive metal containing some metal oxide impurity may yet be used, if an added amount is used to compensate for the resistance of the metal oxide.

The choice of the reactive metal to form the impurity-sensing element should be made on the basis of the following considerations. The metal should react with the critical impurities of choice. The original contaminant of interest is $O_2$. For this impurity, one of the electropositive metals should be used (Group IA, IB, IIA, IIB, and IIIA). The metals should be compatible with the gas stream. Therefore, different metals will be useful in different gas streams. In the case of the inert gas streams, all the metals will be compatible. The metal must not be contaminating. In this case, volatility of the metal or its reaction products is the main concern. Metals such as Cs and Rb may be too volatile to be useful as sensor metals. The metals must not form strongly passivating layers. For example, in the case of aluminum, the formation of a passivating layer might prevent the formation of a deep enough insulating layer to significantly reduce conductivity.

Since in typical high purity processes, the gas stream flowed to the gas purifier contains impurity content on the order of a few tens to a few hundred parts per million, the sensor material should be capable of reacting with and providing a measurable electrical signal in response to the relatively low impurity levels that indicate that the purifier is consumed and impurity breakthrough is commencing. The sensor material should show a rapid and large response to a few tens to a few hundred parts per million concentration of the key impurity.

Properties of some metals that might be used as the sensor material are shown below (from R. C. West, Ed., *CRC Handbook of Chemistry and Physics*, 65th Ed., CRC Press, Inc. Boca Raton, Fla., pp. D155-D159, 1984):

| Metal | Melting Point (°C.) | Vapor Pressure (atm) | E (V) | Forms Passive Oxide? | Reactivity with Inert Gases |
|---|---|---|---|---|---|
| Li | 180.5 | | −3.04 | No | $N_2$ |
| Na | 97.8 | $3 \times 10^{-14}$ | −2.71 | No | None |
| K | 63.7 | $2 \times 10^{-11}$ | −2.93 | No | None |
| Rb | 38.9 | $3 \times 10^{-10}$ | −2.98 | No | None |
| Cs | 28.7 | $3 \times 10^{-9}$ | −2.92 | No | None |
| Mg | 650 | $<10^{-14}$ | −2.37 | Yes | None |
| Ca | 838 | $<10^{-14}$ | −2.87 | ? | None |
| Sr | 768 | $<10^{-14}$ | −4.10 | ? | None |
| Ba | 714 | $<10^{-14}$ | −2.91 | ? | None |
| Al | 660 | $<10^{-14}$ | −1.66 | Yes | None |
| Fe | 1536 | $<10^{-14}$ | −0.45 | No | None |

The metal for the impurity-sensing element for purifiers used in service with inert gases or silanes, such as $H_2$, $N_2$, Ar, He, Ne, Xe, and $SiH_4$, can be chosen from the Group IA or IIA group of metals. Na, Ca, Sr, or Ba are preferred. These metals are soft, have low vapor pressure, are extremely sensitive to $O_2$ and $H_2O$, and are readily and inexpensively available. Note, however, that Li will react with nitrogen and may be unsatisfactory for service in this gas stream. A further consideration is the effect that any trace of the impurity-sensing metal would have on the semiconductor process. From this point of view, metals that do not influence the electrical properties of any vapor-grown layers are preferred, and thus Ba, Ca, and Sr, which have low mobilities in Si, are desirable.

In-line gas purifiers are commonly used to remove traces of moisture from corrosive gases such as hydrogen chloride or chlorine. For the detection of purifier endpoint in these corrosive gases, the sensor material would be selected from those metals that do not react with the corrosive gas except in the presence of water. Iron is a commonly used metal in the form steel in manifold systems. Iron, in the presence of dry HCl and similar gases, is inert. However, in the presence of water, iron rapidly oxidizes to form iron salts. Other transition metals could be used in this application as well, such as those from the Groups IVB and VIB, including titanium, zirconium, hafnium, chromium, molybdenum, and tungsten, and the other metals of Group VIIIB, e.g. cobalt or nickel.

In semiconductor manufacturing operations, water vapor and oxygen are regarded as the critical impurities, whose presence often indicates atmospheric contamination of the process system. Accordingly, the invention will be illustratively described hereinafter primarily with reference to detection of water or oxygen as the impurity species of interest. It will be recognized, however, that such focus is for descriptive purposes only and that the invention is broadly practicable in monitoring of any other impurity species for which a reactive strip or coating material can be found and which will show a conductivity change upon reaction.

If the key impurity is carbon monoxide or carbon dioxide, then the Group IA or IIA metals can serve as the sensor material. These metals react to form carbonates, converting from a high conductivity to a low conductivity state.

The change in resistance that occurs upon reaction of the sensor material with the critical impurity can be a large decrease in resistance. Many gases that are used in semiconductor manufacturing processes are strong reducing agents, e.g., the hydride gases arsine, silane, diborane, phosphine. An appropriate sensor material would be a metal salt that is readily reduced to a lower oxidation state such as the zero-valent metal or metal compound such as a silicide. As an example, consider an inert gas stream in which the key impurity is silane, as for example if back-diffusion from a chemical vapor deposition reactor was of concern. A sensor material formed from mercuric chloride, which has a high resistance, can react with silane will form $Hg^O$, which has a much lower resistance. Likewise, AgCl and CuO would react with silane to become reduced to the $Ag^O$ and $Cu^O$ states respectively, thereby providing a large increase in conductivity (for example, see "Chlorination of silanes by silver chloride," Vanderwielen, A. J.; Ring, M. A.; *Inorg. Chem.*, 11(2), 246–50, 1972; "Halogenation of silanes by silver chloride and silver bromide," Hollandsworth, R. P.; Ingle, W. M.; Ring, Morey A.; *Inorg. Chem.*, 6(4), 844–5, 1967).

For sensor elements whose resistance changes upon reaction with the impurity, the change in resistance should be large, on the order of $10^3$ or more. When conductive metals are used as the sensor material, a useful range may involve a change from a resistance of about 200 $\Omega$ to about 200 K$\Omega$ upon reaction with impurity.

The sensor material may or may not be protected from direct contact with the purifier sorbent material, depending upon the type of purifier and type of sensor material selected. Sensor strips formed from soft metals such as barium or strontium may need to be physically protected from abrasion by purifier resin beads during loading of the purifier vessel, in order to avoid interruption of the conductive pathway. The substrate upon which the sensor material is presented to the gas stream may be recessed and/or guarded by a screen which allows passage of the gas stream but prevents direct contact of the sensor material with the purifier sorbent material.

While the specific structure and function of the endpoint detector systems may be varied within the scope of the present invention, such detection systems must meet various functional criteria, as set out below.

First, the endpoint detector system must itself be non-contaminating in character, with respect to the gas stream being processed. Since the flowing gas stream after its monitoring (and verification of suitably low impurity concentration therein) is flowed to the deposition reactor or other locus of use, any contaminants deriving from the detector system will subsequently be distributed throughout the process system. Any contributed impurities may have a deleterious effect on the products being manufactured. Accordingly, any impurities introduced from the endpoint detector system itself should be suitably low, e.g., in the parts per billion range or lower.

The endpoint detector system must be mechanically tight and leak-free in character. This requirement dictates the use of correspondingly suitable materials of construction in the detector system, with the parts and components of the detector system having a high finish on those parts and components which are in contact with the gas stream, and with all seals of the detector being of a face seal, leak-tight character.

Preferred materials of construction are stainless steel, glass, or chemically resistant epoxies. If any particulates are generated in the use and operation of the endpoint detector, particle filters may be required components of the system. This requirement is readily met in actual practice, since most commercially available gas purifiers incorporate a particle filter as an integral part of the design. The endpoint detector sensing unit should be positioned upstream of the particle filter.

The endpoint detector system should immediately respond to low levels of the critical impurity in the gas stream being purified. Process gas streams employed in the semiconductor manufacturing industry typically contain more than one impurity, and it would be highly advantageous to respond to breakthrough of any of several impurities.

As a practical consideration it may not be possible to find a sensor material that reacts will all impurities. Nevertheless, the sensor material can be expected to respond to broad classes of impurities. For example, a reactive metal such as barium would react with oxygen, water, and other oxidant impurities. Monitoring all impurity species would require a multiplicity of sensor devices, which would in turn unduly complicate the design and operation of the detector system. In practice it is usually possible to identify the key impurities and target endpoint detection at sensing the breakthrough of those substances.

The endpoint detector system should have the requisite sensitivity for detection of gas impurities, preferably on the level of parts per million and most preferably on the level of parts per billion. In semiconductor manufacturing processes, this level of sensitivity is required to distinguish between the unpurified and purified gas streams.

Further, the detector system should be stable when stored for substantial periods of time, e.g., at least six months, and preferably on the order of one year or more, without the sensor element becoming degraded and losing its sensitivity to impurities.

Additionally, the cost of the detector system should be suitably low to ensure ready commercial deployment, with economic, readily available endpoint detector devices being utilizable in present and foreseeable gas purifiers.

The foregoing criteria are accommodated in the broad practice of the present invention by the provision of a detector system in which the gas from the flowing gas stream (either a portion of such stream or the entire stream itself) is passed over a sensor material which is highly reactive with the impurity or impurities of interest, and whose electrical characteristic changes greatly and rapidly upon reaction with the impurity, such electrical characteristic being monitored and visualized outside the purifier by means such as a digital readout meter or via indicator lights that turn on or off as certain current values are reached. Because electrical measurements are capable of great sensitivity, responsiveness to changes in very low levels of impurity can be achieved. The electrical characteristics that are useful in the practice of the present invention are resistance, conductance, and impedance.

The sensor material may be present in the gas stream at a point either within the purifier apparatus or immediately downstream of the purifier apparatus. If the sensor material is present within the purifier, it may be used to show when the front of impurities has reached a point in the purifier that represents a pre-set percentage of the purifier's capacity. For example, it would be useful to know when the purifier was 90% consumed so that the purifier change-out could be planned ahead of time, since process shut-down time might be required.

If the sensor material has been chosen for its ability to react with the impurity to result in a decrease in its conductivity, it must be presented to the gas stream in the form of a thin layer or strip so that the oxidation or other reaction process can penetrate through its entire depth rapidly, so that no conductive pathways will remain. An example of this case is the presentation of a thin strip of reactive Group IA or IIA metal to a gas stream in which the key impurity is oxygen. Alternatively, the a conductive metal continuously coated on a glass fiber could be used as the sensor element. This approach has the advantage that the thickness of the coating, and thus its sensitivity to impurity, can be closely controlled. In any event, a sensor material comprising a conductive metal must be sufficiently homogeneous that a continuous electrically conductive pathway is initially presented to the gas flow stream.

If, on the other hand, the sensor material is a non-conductive material which will become conductive upon reaction with the key impurity, a porous or fibrous morphology may be preferred so that maximum surface area is presented to the gas stream so that conductive pathways will quickly form. An example of this latter case is the presentation of a mass of a metal salt that is readily reduced to a gas stream in which the key impurity is silane. For example, if the sensor material is formed from mercuric chloride, which has a high resistance, reaction with silane will form $Hg^0$, which has a much lower resistance. Likewise, AgCl and CuO would react with silane to become reduced to the $Ag^0$ and $Cu^0$ states respectively, thereby providing a large increase in conductivity.

Regardless of the specific type of impurity sensor material employed in the broad practice of the present invention, the sensor should possess the sensitivity to measure the critical impurity at sufficiently low levels consistent with the high purity character of the gas streams being monitored by the detection system.

The sensor material may be deployed in the detector by a variety of methods. In one embodiment, a thin strip of a reactive metal such as barium or strontium is laid down on an electrically insulating substrate, in direct contact with two electrical leads, which feed through the substrate. The thin strip of reactive metal can be formed by simply drawing a line with a sharpened stick of the reactive metal. The thickness of the metal line can be controlled empirically to achieve the desired initial resistance of approximately 100–500 $\Omega$. The surface of the electrically insulating substrate can be roughened by sanding or grinding to facilitate formation of an adherent film of the reactive metal. Alternatively, layers of metals (e.g., Fe) or metal salts (e.g., AgCl, $HgCl_2$) can be formed by physical and chemical deposition methods such as deposition from solutions, sputtering, chemical or physical vapor deposition, and the like, which are well-known.

The geometry of the layer or mass of sensor material is not critical to the present invention, and may be optimized for each application. Forms such as thin strips or wires with high aspect ratios are generally preferred.

The strip, layer or mass of sensor material should be formed upon a substrate that is inert in the gas stream being purified and monitored. Suitable substrate materials include glass, epoxies, stainless steel, and other materials known to be useful for handling semiconductor process gas streams. The material that forms the feed-through must be sealed to the gas purifier body or the gas line so that no leaks occur. Thermal coefficients of expansion must show a reasonable match so that leaks will not form if large temperature changes occur.

It is preferred to dispose the sensor element laterally in the gas flow stream, with the sensor material strip arranged perpendicularly to the direction of gas flow, thereby avoiding any channeling, by-passing, or other anomalous flow effects.

While the conductivity-based detection system is appropriate for detecting low concentrations of impurity species, large concentration surges may overwhelm the detector system. The detection of a large pulse is achievable by measuring the temperature of the gas purifier scavenger bed or a pad of reactive metal. The temperature change of the bed or pad relative to the outside temperature can be measured. Variations in room temperature can be compensated for. Large exotherms are experienced by gas purifiers of the type exemplified by U.S. Pat. Nos. 4,761,395 or 4,950,419. For example, upon exposure to 12,000 ppm $O_2$, the exotherm exceeded 100° C. in a gas purifier scavenger of the latter type.

Therefore, a 1000 ppm $O_2$ pulse will raise the temperature of a barium metal sensor in excess of 10° C. This temperature rise is due to both local bed heating and oxidation. If the typical impurity surges result in a temperature rise in the nascent resin bed that is insufficiently large to be measured, then a deep "reactive pod" may be included in the system. This reactive pod would contribute to the temperature rise by its heat of reaction with the impurity. The pod material and thin conductor strip are preferably comprised of Ba or Sr or other materials that react exothermically with the impurity.

For the combined conductivity/thermal endpoint detector, four feed through conductors are required. Two carry the electrical signal and two are thermocouples.

Four cases of purifier exhaustion may be efficiently monitored and distinguished by this endpoint detector system.

| Case | Thermocouple | Resistance |
| --- | --- | --- |
| (1) No pulse/front goes through active zone at detector | Room temperature | Low changes to high |
| (2) Large pulse but does not reach purifier at end point sensor | May or may not detect exotherm | Low |
| (3) Large pulse/pulse goes through active zone at detector | Exotherm detected | Low changes to high |
| (4) Large pulse/pulse goes through deactivated zone at | Exotherm no detected | High with no change |

-continued

| Case | Thermocouple | Resistance |
|---|---|---|
| detector | | |

In the first case, no large pulse of impurities occurs. The impurity-scavenging bed becomes consumed to the location of the endpoint sensor. No exotherm is observed and the resistance changes from low to high. The purifier should be changed out at this time.

In the second case a large impurity pulse comes through the bed but does not reach the endpoint sensor. The resistance will remain in the low state. An exotherm may or may not be detected. If the exotherm is detected, an alarm may be actuated. In this case, the purifier has done its job and prevented the pulse from reaching the rest of the process equipment.

In the third case, a large pulse of impurity engulfs the endpoint sensor. Both the temperature and normal endpoint alarms will be actuated. At this point the user should isolate the semiconductor processing system to prevent contamination of the process piping.

In the fourth case, the system should not alarm. However, the purifier should have been changed out during case one.

Referring now to the drawings, FIG. 1 shows a schematic of an endpoint detector system 100 according to one embodiment of the present invention. Sensor material 101 is laid down in a thin strip on insulating substrate 106, and held in connection with feedthroughs 107 and 108 by conductive pads 104 and 105, screwed down by screws 102 and 103. The electrical signal is passed through leads that are within the feedthroughs, connecting to the controller means that is external to the purifier.

Figure 2:
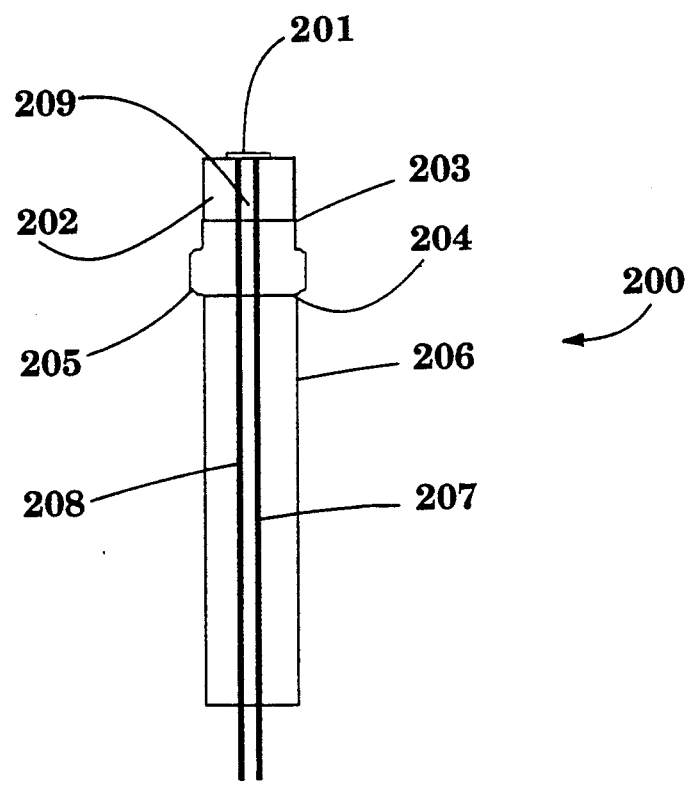
FIG. 2 shows a schematic of a feedthrough assembly that can be used to insert the endpoint detector into the housing of a gas purifier.

FIG. 2 shows a schematic of the feed-through system 200 that can be used to insert the endpoint detector into the housing of a gas purifier or into a gas line. Sensor material 201 is laid down in a thin strip on insulating substrate 202, through which pass the electrical leads 207 and 208 which provide an electrical connection from the sensor material to an external means for display or for effecting the opening or closing of a relay. Transition seal 203 provides a gas-tight seal between the glass tube 205 and the insulating substrate 202, and transition seal 204 provides a gas-tight seal between the glass tube 205 and the tube 206 which contains the feedthrough electrical leads 207 and 208 and which passes out of the purifier or gas line. The area 209 enclosed by glass tube 205 and through which the leads 207 and 208 pass may be filled with a potting compound.

In the practice of the invention, insulating substrate 202 may be a ceramic material. Ceramics are desirable because of their inertness and impermeability to gases. Transition seal 203 may be a glass-ceramic transition seal, and 204 may be a glass-metal transition seal. Such seals are capable of being made gas-tight and, because they are formed by fusing the glass, do not introduce any foreign materials that could contaminate the gas stream. Structural reinforcement may be provided to glass tube 205 by filling it with a potting compound such as an epoxy resin, silicone, polyurethane, or other similar thermosetting polymer which forms a good seal to glass. Such inert, physically strong, and electrically insulating polymers are well-known and are exemplified by Torr-Seal, sold by Varian Co. The tube 206 should be formed of a material that is physically strong and chemically inert in the gas stream being purified. Since most gas purifiers are constructed of metal, in particular stainless steel, metal is the preferred material of construction for 206. Suitable materials include tungsten, Inconel, Hastelloy and, most preferably, stainless steel. The feedthrough electrical leads 207 and 208 should be formed from a conductive material such as copper or other metals. Because of their superior thermal match with glass, tungsten or nickel alloys such as Kovar are preferred, although, since copper is more convenient to work with, a tungsten or Kovar lead might be connected to a copper wire after it exited from the purifier body.

Figure 3:
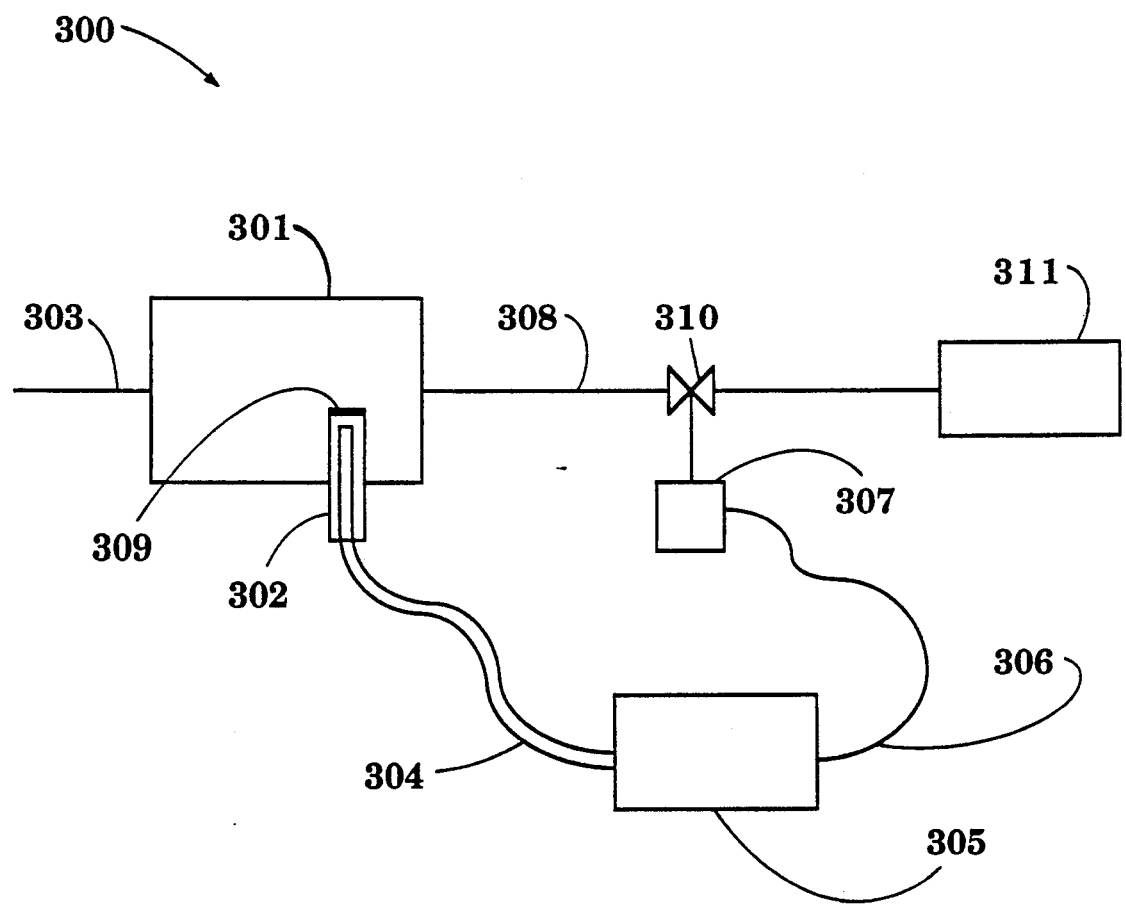
FIG. 3 shows a schematic of the endpoint detector used with an inline gas purifier.

FIG. 3 shows a schematic of the endpoint detector assembly 302 used with an inline gas purifier 301. Incoming gas flows into the gas purifier via gas supply line 303. The impurity level is sensed by endpoint detector sensor material 309, which is exposed to the gas stream within the purifier 301. Joined to the endpoint detector in signal transmitting and receiving relationship, via signal line 304, is a controller 305. This controller may include optoelectronic converters, digital/analog circuitry, etc., by means of which the sensing of impurity species by the endpoint detector 302 is convertible to a processing signal. This processing signal is transmitted by signal transmitting means 306 to a valve control mechanism 307, which mechanically closes a valve 310 connecting the gas supply line 308 to the downstream processing facility 311, e.g. a chemical vapor deposition reactor. If a sufficient amount of the critical impurity species reacts with the sensor material 309, the conductivity change will trigger valve closing via the controller.

Figure 4:
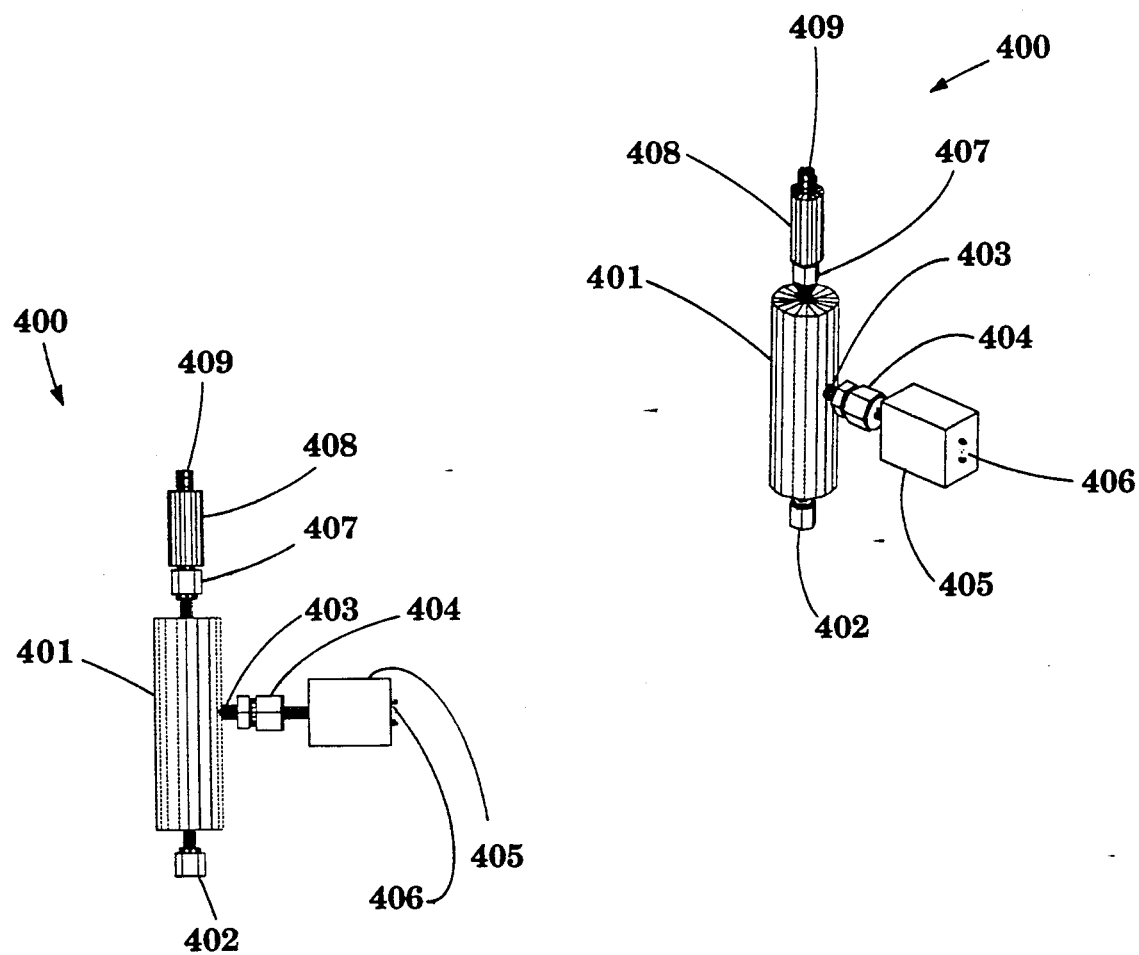
FIG. 4 shows the endpoint detector connected through a sensor port constructed in the body of an inline gas purifier.

FIG. 4 shows two perspective views of a purification system 400, comprising an endpoint detector connected through a sensor port 403 constructed in the body of an inline gas purifier 401 connected to a downstream particle filter 408. The gas flow stream to be purified enters the purifier through the inlet 402. The sensor port 403 is constructed in the purifier body, presenting the sensor element to the gas flow stream. The detector feedthroughs pass through the sensor port 403 and are connected via a fitting 404 to the detector control module 405, which provides LED display 406. The gas flow stream continues through the connection fitting 407, passing through particle filter 408 and finally exiting through outlet 409.

In semiconductor manufacturing, many of the gases used are toxic or flammable, and all must be of exceptionally high purity. Therefore, in the practice of the present invention, all connections and fittings, 402, 404, 407, and 409, must be of high integrity and non-contaminating, such as VCR or Swagelok fittings. The LED display 406 may be configured in a variety of ways for a particular purification system; a useful set-up displays a green light when the detector does not sense impurity, a yellow light as the detector senses a very low level of impurity and its electrical characteristic is beginning to change, and a red light when the electrical characteristic has undergone its full transition, keyed to the exhaustion of the purifier sorption bed adjacent to the detector.

In some gas purifiers with which the inline detector might be used, the particle filter is constructed as an integral part of the purifier rather than as a distinct unit connected downstream. In this case, the sensor port would be disposed upstream of particle filtration.

Figure 5:
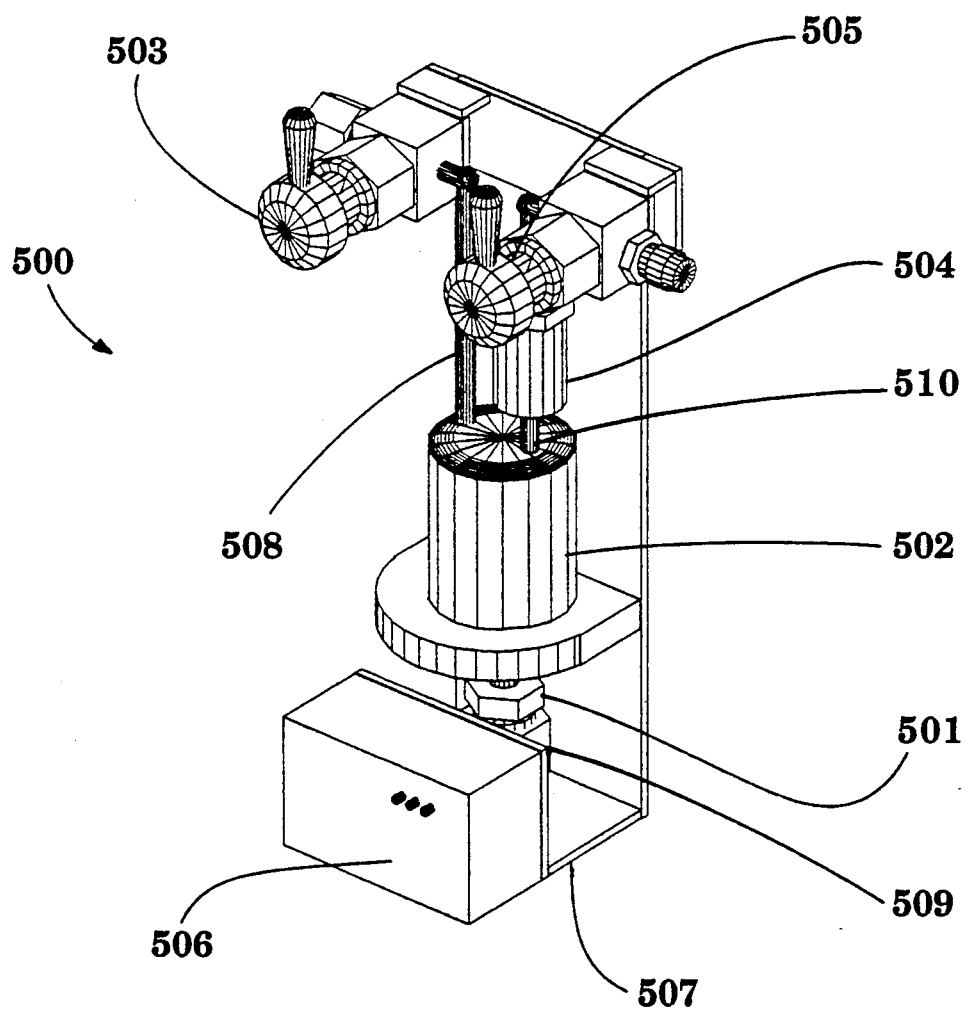
FIG. 5 shows the endpoint detector connected through the fill port of an inline gas purifier.

FIG. 5 shows a perspective view of a system 501 which has an endpoint detector conveniently connected through the fill port of an inline gas purifier 502. Valve 503 controls the flow of gas into the gas purifier 502 through gas line 508. The endpoint detector 509 is connected through the fill port 501. Gas flows out of the purifier through gas flow line 510 and passes through particle filter 504 before exiting the system. Valve 505 controls the flow of gas out of the system. The endpoint detector is connected electrically to signal conditioner module 506, which is fastened to a supporting member 507, upon which the whole purifier system also rests.

Figure 6:
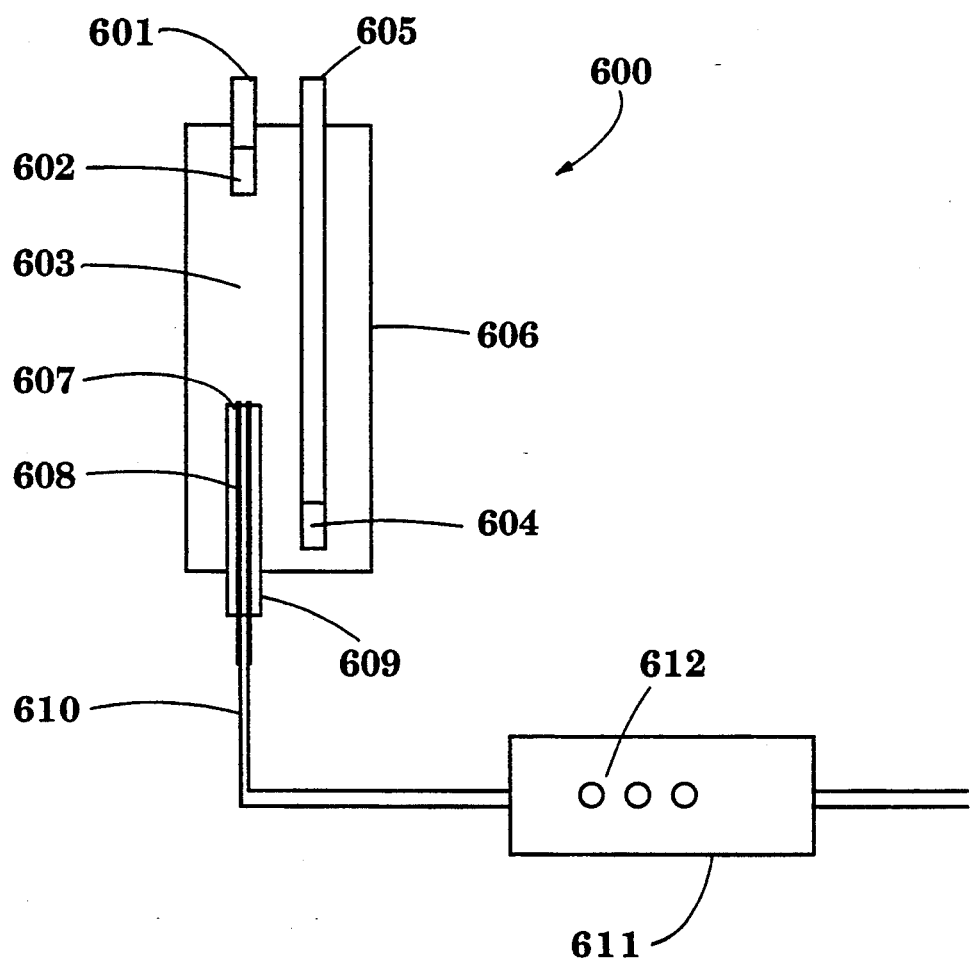
FIG. 6 shows a schematic cross section of a purifier system similar to the one shown in perspective in FIG. 5, employing an endpoint detector.

FIG. 6 shows a schematic cross section of a purifier system similar to the one shown in perspective in FIG. 5, employing an endpoint detector. The gas flow stream enters the purifier 606 through gas line 601, passing through porous frit 602 which prevents the sorbent purification media 603 from clogging the lines. The gas flows over sensor material 607, which is in electrical contact with leads 608. Leads 608 pass through feed through tube 609 and are in electrical connection with wires 610 which lead to the signal conditioning module 611, which has visual display signals 612. Leads 613 from the signal conditioning module may be used to actuate valve controllers or alarms. The gas flows out of the purifier through porous frit 604 and gas line 605. In this embodiment of the present invention, the gas contacts the sensor material after it has passed through most of the purifier sorbent material and just before it exits the purifier system.

Figure 7:
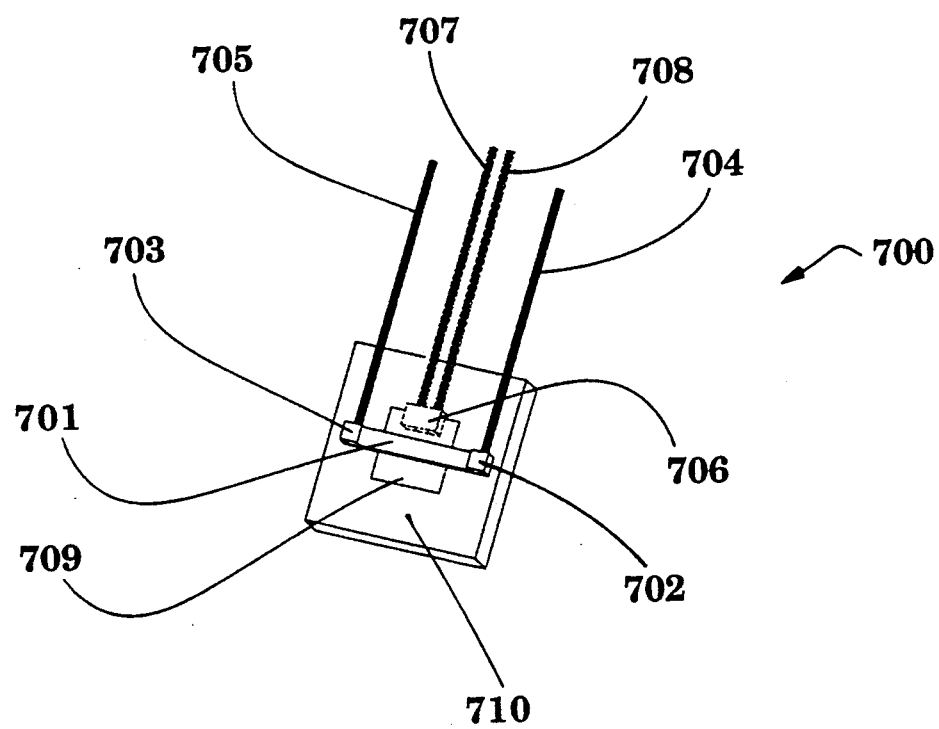
FIG. 7 shows a schematic of the configuration of one embodiment of the detector/thermocouple version of the present invention.

FIG. 7 shows a schematic of the configuration of one embodiment of the detector/thermocouple version of the present invention. The detector/thermocouple system 700 has a block of material 706 which has high thermal conductivity connected by thermocouple leads 707 and 708 to an external temperature readout means (not shown). The thermally conductive material 706 rests on a deep reactive pod 709, which also supports the thin strip of sensor material 701. The sensor material 701 is connected via screws 702 and 703 to electrical leads 704 and 705 which connect to an external conductivity display means (not shown) and/or a means for opening or closing a relay.

Figure 8:
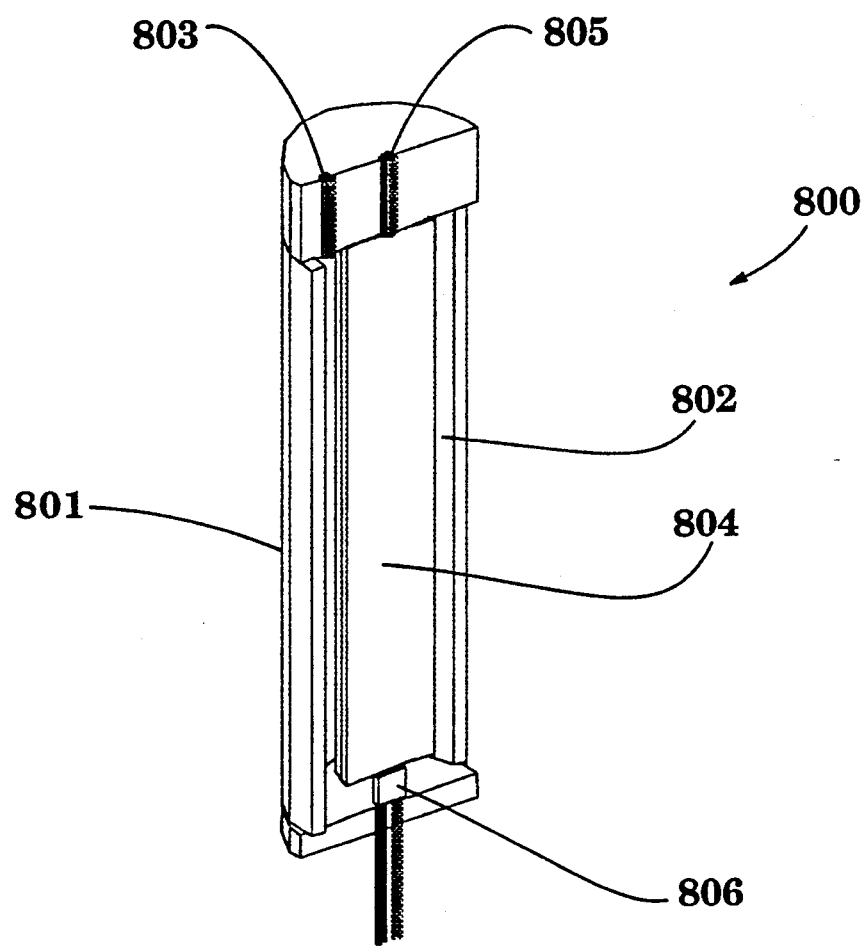
FIG. 8 is a schematic depiction of a configuration of the detector/thermocouple system of the present invention in use with a gas purifier.

FIG. 8 is a schematic depiction of a configuration of the detector/thermocouple system 800 of the present invention in use with a gas purifier 801. The gas flow stream enters through port 803 and is routed initially through the annular space 802, where it contacts the purifier sorbent material. The gas flow stream returns up the center dip tube 804, which also may be loaded with purifier sorbent material, and exits through port 805. The ratio between the center dip tube diameter and the inner diameter of the purifier controls the volume of the purifier sorbent material that the gas flow stream will contact before encountering the endpoint sensor 806, which is disposed at the opening to the center dip tube. The endpoint sensor 806 is of the type shown in FIG. 7.

Figure 9:
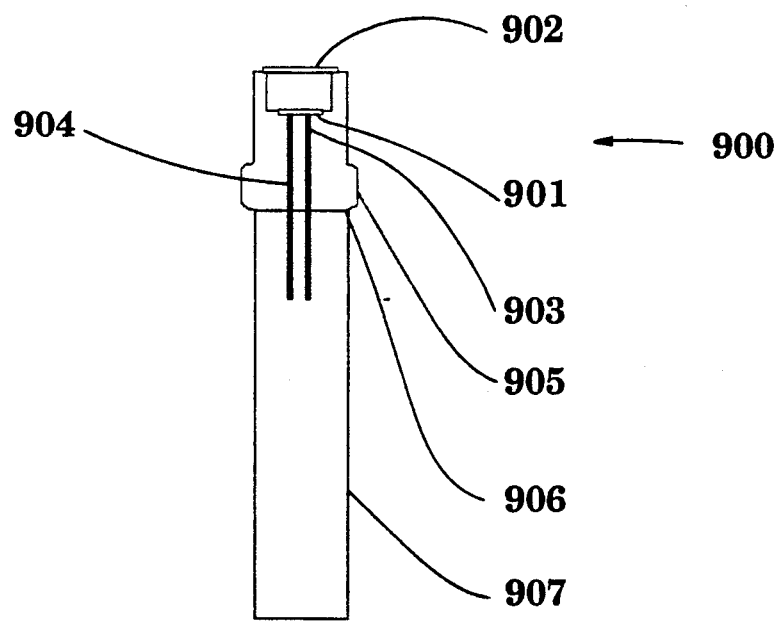
FIG. 9 shows a schematic of one embodiment of the endpoint detector system wherein the sensor element is recessed and protected by a screen.

FIG. 9 shows a schematic of one embodiment of the endpoint detector system 900 wherein the sensor material 901 is recessed and protected by a screen 902. The sensor material 901 is in electrical connection with leads 903 and 904, which pass through the glass tube 905, which is sealed by a transition seal 906 to the metal feed through tube 907.

Figure 10:
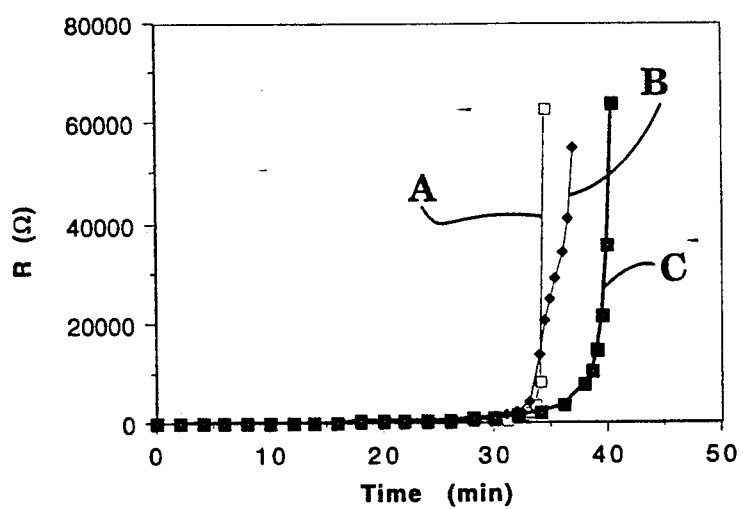
FIG. 10 shows the change in resistance of a thin barium strip in response to exposure to oxygen in the gas stream.

FIG. 10 is a graph of resistance in ohms of a thin barium strip (of thickness estimated at approximately 10–50 μm prepared by drawing a barium line on the insulating substrate with a barium pencil) versus time in minutes during exposure to 13 ppm oxygen in a helium gas stream. A, B, and C represent three separate runs.

Figure 11:
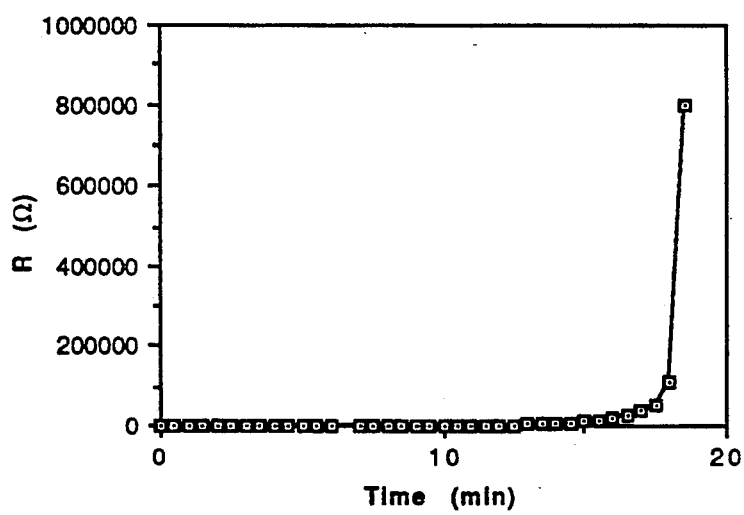
FIG. 11 shows the change in resistance of a thin strontium strip in response to exposure to oxygen in the gas stream.

FIG. 11 is a graph of resistance in ohms of a thin strontium strip (of thickness estimated at approximately 10–50 μm) versus time in minutes during exposure to 13 ppm oxygen in a helium gas stream. FIGS. 4 and 5 show that when the reactive metal becomes oxidized to a certain extent, conductivity is interrupted and the resistance increases dramatically.

Figure 12:
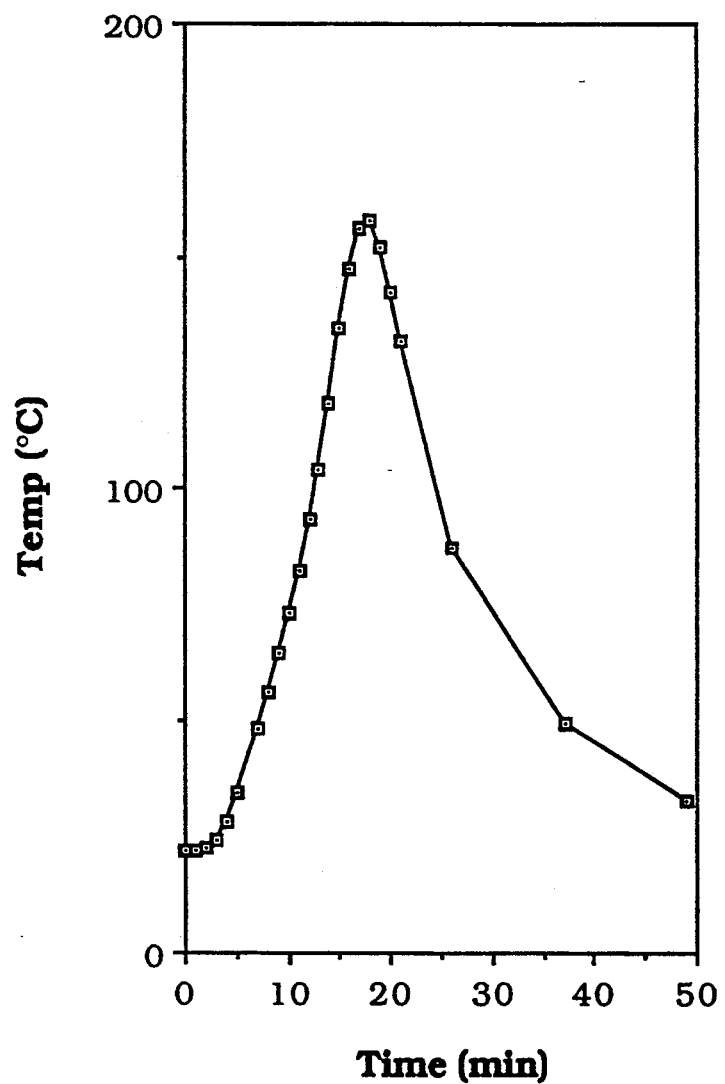
FIG. 12 shows the temperature response of the detector to a pulse of oxidizing impurity.

FIG. 12 shows the temperature response in degrees centigrade of the detector to a pulse of oxidizing impurity.

If the concentration of the critical impurity species is sufficiently low, the sensor material remains substantially unchanged. If, however, the impurity concentration rises, the conductivity changes. The resulting electrical signal is carried to a display means and/or to a means for opening or closing a relay, thereby triggering a step such as valve closing or valve opening that is required to protect the semiconductor manufacturing process from the deleterious effects of the increase in impurity concentration.

Referring to FIG. 3, the endpoint detector with a sensor element comprising a thin strip of reactive barium metal may be used in a gas stream purifier that removes oxygen, water, and other oxidant impurities from nitrogen used in a gas cabinet purge system. Nitrogen, containing 10–100 ppm of impurity flows from gas supply line 303 into the gas purifier 301, which is of the type disclosed in U.S. Pat. No. 4,950,419, where the purifier sorbent material chemisorbs impurities down to a level of 10 ppb or less in the gas stream. If the purifier sorbent material becomes spent, the concentration of oxygen, water, and other oxidant impurities increases and they react with the barium sensor material. The conductivity of the barium sensor material decreases dramatically. Its resistance changes from about 200 $\Omega$ to about 200 K$\Omega$, and the controller 305, in response to the changed electrical signal from leads 304, activates the valve closing mechanism 307, protecting the process in reactor 311 from exposure to impurity.

In this same example, if arsine back-diffuses from reactor 311, the reactive barium metal sensor reacts to form barium arsenide, and the conductivity again decreases dramatically. Again, the controller 305, in response to the changed electrical signal from leads 304, activates the valve closing mechanism 307, protecting the gas supply lines from contamination with arsine, a hazardous gas.

Other gas flow streams in which the endpoint detector of the present invention can provide analogous service include nitrogen flow streams used to pressurize liquid reagents and solvents for delivery into semiconductor processes and the various types of chemical vapor deposition processes that not only require extremely high gas purity but also use gases such as arsine, silane or phosphine that are toxic and/or flammable.

Although the invention has been described with respect to particular features, aspects, and embodiments thereof, it will be apparent that numerous variations, modifications, and other embodiments are possible within the broad scope of the present invention, and accordingly, all variations, modifications, and embodiments are to be regarded as being within the spirit and scope of the invention.

What is claimed is:

1. An endpoint detector system for sensing the presence of an impurity component in a gas flow stream passed through a vessel containing a bed of a sorbent material selective for sorbing said impurity component, at a selected locus in the bed, said detector system comprising:
   a sensor element disposed at said selected locus of the sorbent material bed, and comprising a line from about 10 to about 50 micrometers thickness and formed of a material which is reactive with the impurity component to yield a reaction product of changed electrical characteristic; and
   means operatively coupled to the sensor element for providing an output indicative of the changed electrical characteristic of the sensor element upon reaction of the sensor element material with the impurity component of a gas stream flowed through the sorbent material bed.

2. A detector system according to claim 1, wherein the electrical characteristic is selected from the group consisting of electrical conductivity, electrical resistance, and electrical impedance characteristics.

3. A detector system according to claim 1, wherein the material of the sensor element comprises a metal selected from the group consisting of Group IA metals, Group IIA metals, and mixtures, alloys, and combinations thereof.

4. A detector system according to claim 1, wherein the material of the sensor element comprises an electrically conductive metal selected from the group consisting of sodium, potassium, calcium, strontium, and barium, and mixtures, alloys, and combinations thereof.

5. A detector system according to claim 1, wherein the material of the sensor element consists essentially of elemental metal selected from the group consisting of Group IA metals, Group IIA metals, and mixtures, alloys, and combinations thereof.

6. A detector system according to claim 1, wherein the means coupled to the sensor element, for providing an output indicative of a changed electrical characteristic of the sensor element upon reaction of the sensor element material with the impurity component of the gas stream, produces an output control signal when the electrical characteristic of the sensor element changes by a predetermined extent.

7. A detector system according to claim 1, wherein the electrical characteristic is electrical conductivity.

8. A detector system according to claim 1, wherein the sensor element comprises a conductive metal.

9. A detector system according to claim 1, wherein the material of the sensor element comprises a metal selected from the group consisting of iron, titanium, zirconium, hafnium, chromium, molybdenum, nickel, and tungsten and mixtures, alloys, and combinations thereof.

10. A detector system according to claim 1, wherein the sensor element material comprises a metal-containing composition which is reducible in the presence of a reducing agent impurity component to yield as a reduction reaction product a conductive metal of changed electrical conductivity relative to the electrical conductivity of the metal-containing composition.

11. A detector according to claim 1, wherein the electrical characteristic is electrical impedance, and the output means comprise an alternating current circuit joined in circuit relationship to the sensor element and comprising an impedance output indicating means responsive to the impedance characteristic of the sensor element.

12. A detector system according to claim 1, wherein the electrical characteristic is electrical conductivity, and the output means comprise a direct current circuit joined in circuit relationship to the sensor element and comprising a conductivity output indicating means responsive to the conductivity characteristic of the sensor element.

13. An endpoint detector system for sensing the presence of an impurity component in a gas flow stream passed through a vessel containing a bed of a sorbent material selective for sorbing said impurity component, at a selected locus in the bed, said detector system comprising:
   a first sensor element disposed at said selected locus of the sorbent material bed, and comprising a material which is reactive with the impurity component to yield a reaction product of changed electrical characteristic;
   means operatively coupled to the first sensor element for providing an output indicative of the changed electrical characteristic of the first sensor element upon reaction of the first sensor element material with the impurity component of a gas stream flowed through the sorbent material bed;
   a second, thermal sensor disposed in the bed of sorbent material; and
   thermal output means operatively coupled to the second, thermal sensor for providing an output indicative of temperature change in the bed of sorbent material.

14. A detector system according to claim 13, further comprising means for detecting large concentration surges of impurity component in the bed of sorbent material, including a pad of material which is exothermically reactive with the impurity component, with said second, thermal sensor being operatively coupled to the pad, whereby upon passage of a large concentration surge of impurity component through the bed, the pad of exothermically reactive material will exothermically react therewith, and the second, thermal sensor will correlatively actuate the thermal output means to indicate said large concentration surge.

15. A detector system according to claim 1, wherein the sensor element line is arranged perpendicularly to the direction of flow of the gas stream through the bed of sorbent material.

16. A detector system according to claim 1, wherein the change in electrical characteristic of the sensor element upon reaction of the sensor element material with the impurity component of the gas stream flowed through the sorbent material bed, is a change of at least $10^3$ times, in relation to the initial electrical characteristic value.

17. A detector system according to claim 1, wherein the sensor element material comprises an electropositive metal compatible with the gas stream and selected from the group consisting of Group IA, IB, IIA, IIB, and IIIA metals.

18. A detector system according to claim 1, wherein the output means comprise visual and/or audible output display means.

19. A detector system according to claim 1, further comprising a second sensor element comprising a material which is reactive with a same or different impurity component to yield a reaction product of changed electrical character from the sensor element initial material, disposed at a second locus in the sorbent material bed, in spaced relationship to the first sensor element, and means coupled to the second sensor element for providing an output indicative of changed electrical character of the second sensor element upon reaction with same or different impurity component.

20. A method of sensing the presence of an impurity component in a gas flow stream passed through a gas flow stream purifier vessel containing a bed of a sorbent material selective for said impurity component, at a selected locus in the bed, said method comprising:
disposing a sensor element comprising a line from about 10 to about 50 micrometers thickness and formed of a material which is reactive with the impurity component to yield a reaction product of changed electrical characteristic, at said selected locus in the sorbent material bed;
monitoring the electrical characteristic of the sensor element; and
in response to a change in the electrical characteristic upon reaction of the sensor element material with impurity component of a gas stream flowed through the sorbent material bed, providing an output indicative of changed electrical characteristic of the sensor element.

21. A method according to claim 20, wherein the electrical characteristic is selected from the group consisting of electrical conductivity, electrical resistance, and electrical impedance characteristics.

22. A method according to claim 20, wherein the material of the sensor element comprises a metal selected from the group consisting of Group IA metals, Group IIA metals, and mixtures, alloys, and combinations thereof.

23. A method according to claim 20, wherein the material of the sensor element comprises a metal selected from the group consisting of sodium, calcium, strontium, and barium, and mixtures, alloys, and combinations thereof.

24. A method according to claim 20, wherein the material of the sensor element consists essentially of elemental metal selected from the group consisting of Group IA metals, Group IIA metals, and mixtures, alloys, and combinations thereof.

25. A detector system according to claim 20, wherein the electrical characteristic is electrical conductivity.

26. A method according to claim 20, wherein the sensor element material comprises a conductive metal.

27. A method according to claim 20, wherein the sensor element material comprises a metal-containing composition which is reducible in the presence of a reducing agent impurity component to yield as a reduction reaction product a conductive metal of changed electrical conductivity relative to the electrical conductivity of the metal-containing composition.

28. A method according to claim 20, further comprising monitoring the temperature of a selected locus of the sorbent material bed and responsively generating an output indicative of a temperature change in the bed of sorbent material.

29. A method according to claim 20, further comprising terminating the flow of the gas stream through the bed of sorbent material when the electrical characteristic of the sensor element changes by a predetermined extent.

30. A method according to claim 20, wherein the sensor element material comprises an electropositive metal compatible with the gas stream and selected from the group consisting of Group IA, IB, IIA, IIB, and IIIA metals.

31. A method according to claim 20, further comprising disposing at a second locus in the sorbent material bed, in spaced relationship to the first sensor element a second sensor element comprising a material which is reactive with a same or different impurity component to yield a reaction product of changed electrical character from the sensor element initial material, and providing an output indicative of changed electrical character of the second sensor element upon reaction with said same or different impurity component.

32. A method according to claim 20, wherein the impurity component comprises a member selected from the group consisting of water, oxygen, and mixtures thereof.

33. A method according to claim 32, wherein the sensor element material is selected from the group consisting of sodium, potassium, calcium, strontium, and barium.

34. A method according to claim 20 according to claim 1, wherein the material of the sensor element comprises a metal selected from the group consisting of iron, titanium, zirconium, hafnium, chromium, molybdenum, nickel, and tungsten and mixtures, alloys, and combinations thereof.

* * * * *